(12) United States Patent
Ouwerkerk et al.

(10) Patent No.: US 10,617,341 B2
(45) Date of Patent: Apr. 14, 2020

(54) PROCESSOR FOR PROCESSING SKIN CONDUCTANCE DATA AND DEVICE FOR DETECTING AT LEAST ONE STAGE OF BURNOUT AND/OR CHRONIC FATIGUE SYNDROME OF A LIVING BEING

(71) Applicant: KONINKLIJKE PHILIPS N.V., Eindhoven (NL)

(72) Inventors: Martin Ouwerkerk, Eindhoven (NL); Joanne Henriette Desiree Monique Westerink, Eindhoven (NL); Alphons Antonius Maria Lambertus Bruekers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 423 days.

(21) Appl. No.: 15/100,050

(22) PCT Filed: Nov. 21, 2014

(86) PCT No.: PCT/EP2014/075217
§ 371 (c)(1),
(2) Date: May 27, 2016

(87) PCT Pub. No.: WO2015/082231
PCT Pub. Date: Jun. 11, 2015

(65) Prior Publication Data
US 2017/0000398 A1 Jan. 5, 2017

(30) Foreign Application Priority Data
Dec. 5, 2013 (EP) .................................... 13195788

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0533* (2013.01); *A61B 5/7239* (2013.01); *A61B 5/7275* (2013.01); *G16H 50/20* (2018.01)

(58) Field of Classification Search
CPC ..................................................... A61B 5/165
See application file for complete search history.

(56) References Cited

U.S. PATENT DOCUMENTS

2010/0026984 A1* 2/2010 Lewis ................... G01S 7/4811
356/5.01
2011/0245633 A1 10/2011 Goldberg et al.

FOREIGN PATENT DOCUMENTS

WO 2012140537 A1 10/2012
WO 2013076615 A1 5/2013

OTHER PUBLICATIONS

M. Kusserow, "Stress Arousal Monitoring in Natural Environments", A dissertation submitted to ETH Zurich for the degree of Doctor of Sciences, 2012, 204 pages.
(Continued)

*Primary Examiner* — Daniel L Cerioni
*Assistant Examiner* — Yasmeen S Warsi

(57) ABSTRACT

The present invention relates to a processor for processing skin conductance data of a living being, comprising an input unit (12) for receiving a skin conductance data signal (13) comprising a plurality of data peaks, a calculating unit (14) for computing a skin conductance peak data signal over a long-term period by deriving a feature related to said data peaks from said skin conductance data signal (13) and forming a summation of said feature per time unit and an analyzing unit (16) for analyzing an average and/or an absolute value of said skin conductance peak data signal
(Continued)

over at least a portion of said period to get information on at least one stage of burnout and/or chronic fatigue syndrome of said living being.

17 Claims, 4 Drawing Sheets

(51) Int. Cl.
    *A61B 5/053*     (2006.01)
    *G16H 50/20*     (2018.01)

(56) References Cited

OTHER PUBLICATIONS

Demitrack, et al., "Evidence for impaired activation of the hypothalamicpituitary-adrenal axis in patients with chronic fatigue syndrome", PubMed, 1991 (abstract).

Demitrack, et al., "Evidence for and pathophysiologic implications of hypothalamic-pituitary-adrenal axis dysregulation in fibromyalgia and chronic fatigue syndrome", Ann NY Acad Sci, May 1, 1998; 840:684-97 (abstract).

Glaser, et al., Stress-induced immune dysfunction:implications for health, Nature Reviews—Immunology 5 (2005) 243 (abstract).

Grossia, et al., "Physiological correlates of bournout among women", J. Psychosomatic Research 55 (2003) 309 (abstract).

Heim, et al., "The potential role of hypocortisolism in the pathophysiology of stress-related bodily disorders", Psychoneuroendocrinology, 25, (2000) (abstract).

Kudielka, et al., "Why do we respond so differently? Reviewing determinants of human salivary cortisol responses to challenge", Psychoneuroendocrinology 34 (2009) (abstract).

Langelaan, et al., "Do burned-out and work-engaged employees differ in the functioning of the hypothalamic-pituitary-adrenal-axis?", Scandinavian Journal of Work, Environment & Health, vol. 32, No. 5 (Oct. 2006), pp. 339-348.

Langelaan, et al., "Is Burnout Related to Allostatic Load?" International Journal of Behavioral Medicine 2007, vol. 14, No. 4, pp. 213-221.

McEwen, "Central effects of stress hormones in health and disease: Understanding the protective and damaging effects of stress and stress mediators", Eur J. Pharmacol, Apr. 7, 2008; 583(2-3): 174-185.

McEwen, Protective and Damaging Effects of Stress Mediators, New England Journal of Medicine 1998, vol. 338, pp. 171-179 (abstract).

Meyer, et al., "Minireview: Hair Cortisol: A Novel Biomarker of Hypothalamic-Pituitary-Adrenocortical Activity", Endicronology, Sep. 2012, 153(9); pp. 4120-4127.

Hellhammer, et al., "Stress The Brain-Body Connection", Key Issues in Mental Health, vol. 174, Feb. 20, 2008 (abstract).

Sonnentag, "Burnout and functioning of the hypothalamus-pituitary-axis-there are no simple answers", Scandinavian J. of Work Environmental & Heatlh, vol. 32, (2006), pp. 333-337 (abstract).

Sterling et al "Allostasis: A New Paradigm to Explain Arousal Pathology" Handbook of Life and Stess, Cognition and Health Edited by S. Fisher and J. Reason (1988).

\* cited by examiner

PROCESSOR FOR PROCESSING SKIN CONDUCTANCE DATA AND DEVICE FOR DETECTING AT LEAST ONE STAGE OF BURNOUT AND/OR CHRONIC FATIGUE SYNDROME OF A LIVING BEING

CROSS-REFERENCE TO PRIOR APPLICATIONS

This application is the U.S. National Phase application under 35 U.S.C. § 371 of International Application No. PCT/EP2014/075217, filed on Nov. 21, 2014, which claims the benefit of European Patent Application No. 13195788.8 filed on Dec. 5, 2013. These applications are hereby incorporated by reference herein, for all purposes.

FIELD OF THE INVENTION

The present invention relates to a processor and a processing method for processing skin conductance data of a living being as well as a computer program implementing such method. The present invention further relates to a device for detecting for detecting at least one stage, in particular an early stage, a full stage and/or a recovery stage, of burnout and/or chronic fatigue syndrome of a living being comprising such a processor, as well as to a corresponding method.

BACKGROUND OF THE INVENTION

In today's modern society, a large portion of the population encounter stress in their life from time to time. As a response to the stress, the human body produces stress hormones. The essential effects of the stress hormones have two different aspects as described in McEwen et al., "Central effects of stress hormones in health and disease: Understanding the protective and damaging effects of stress and stress mediators", European Journal of Pharmacology 583 (2008), p. 174-185. On the one hand, the body responds to almost any sudden, unexpected event by releasing chemical mediators. Such chemical mediators are for example catecholamines that increase the heart rate and the blood pressure, thus can help the individual cope with the situation. On the other hand, chronic elevation of such mediators, including chronically increased heart rate and blood pressure, produce chronic wear and tear on the cardiovascular system.

The human body responds to daily events by an active process known as allostasis. The term allostasis has been introduced in Fischer et al., "Allostasis: a new paradigm to explain arousal pathology", Handbook of Life Stress, Cognition and Health, John Wiley & Sons, New York (1988), p. 629-649. The terms allostatic load and allostatic overload refer to the wear and tear that results from either too much stress or from inefficient management of allostasis, for example not turning off in response when it is no longer needed.

The stress response or stress behavior of persons with diseases such as burnout or chronic fatigue syndrome is of particular relevance for the field of endocrinology. A stressor activates the hypothalamus, which releases the corticotrophin releasing hormone (CRH). This hormone activates the pituitary gland, which releases the endrocorticaltropic hormone (ACTH), which activates the adrenal gland. This results in the release of glucolcorticoid hormones, such as cortisol. The afore-mentioned mechanism is also known under the Hypothalamus-Pituitary-Adrenal axis (HPA-axis), which plays an important role in the stress response in human bodies.

The activity of the HPA-axis is thus tightly linked to the stress response of an individual. In the case of burnout, both an initial hyperactivity and a hypoactivity of the HPA-axis have been reported. Since the hyper- and hypoactivity of the HPA-axis can be investigated based on the cortisol level, they are also referred to as hypercortisolism and hypocortisolism, respectively. Heim et al., "The potential role of hypocortisolism in the pathophysiology of stress-related bodily disorders", Psychoneuroendocrinology, 25 (2000) 1-35, describes how an initial hyperactivity of the HPA-axis develops into a hypoactivity as a response to chronic stress. This means that early burnout symptoms may be signaled by a hyperactivity of the HPA-axis, which in turn can be signaled by high salivary cortisol levels.

US 2012/0289790 A1 discloses a method including accessing data streams from a mood sensor and one or more of a heart-rate monitor, a blood pressure monitor, a pulse oximeter or an accelerometer monitoring a person, analyzing data sets collected from the person when the person is stressed and unstressed, analyzing data sets, and determining a current stress index of the person based on the analysis. It also discloses a system corresponding to the method.

SUMMARY OF THE INVENTION

It is an object of the present invention to provide a device and a method which enable an early and reliable detection of an upcoming burnout and/or chronic fatigue syndrome of a living being so that a corresponding warning can be issued.

In a first aspect of the present invention, a processor for processing skin conductance data of a living being is presented, the processor comprising an input unit for receiving a skin conductance data signal comprising a plurality of data peaks, a calculating unit for computing a skin conductance peak data signal over a period of at least one day by deriving a feature related to said data peaks from said skin conductance data signal and forming a summation of said feature per time unit; and an analyzing unit for analyzing an average and/or an absolute value of said skin conductance peak data signal over at least a portion of said period to get information on at least one stage of burnout and/or chronic fatigue syndrome of said living being, wherein said analyzing unit is configured to compare the average and/or absolute value of said skin conductance peak data signal against two different thresholds, and an output unit configured to output a full stage signal indicating a full stage of said predetermined stress state when the average and/or absolute value of said skin conductance peak data signal falls below a lower threshold after it has exceeded said upper threshold, and/or a recovery stage signal indicating a recovery stage when the average and/or absolute value of said skin conductance peak data signal rises towards and/or exceeds said lower threshold without exceeding said upper threshold after said full stage of said predetermined stress state, and/or a healthy state signal, when the average and/or absolute value of said skin conductance peak data signal is above said lower threshold and below said upper threshold.

Skin conductance is a particularly advantageous property of a living being, such as a human, in order to extract information about his/her stress response. It is well known that activities of the HPA-axis including hyper- and hypoactivity are in physiological and/or endocrinological correlation with the conductance of skin. In particular, these activities are in correlation with the skin in various body locations, such as the palmar region of the hands, the sole of the feet, as well as the volar region of the wrist and the ankles Data peaks in the skin conductance data signal thus provide important accesses to changes and/or tendencies of the living being's stress response. Such data peaks thus comprise usually a plurality of features, including without limitation rising edges, rise time, peak heights, number of peaks. Hence, it is particularly advantageous to derive a feature related to the data peaks and form a summation of the feature per time unit. In this way, the progressing of the derived feature can be tracked over the long-term period, so that the living being's stress response can be quantitatively followed.

The thresholds can be determined based on long-term analysis of the stress response of the living being. Alternatively, clinical references can also be used. The processor advantageously enables a reliable stress-analysis.

In the fields relevant to the present invention, a long-term period is a time window which extends over at least a portion of a typical development stage of a stress state including burnout and chronic fatigue syndrome. Usually, a skin conductance peak data signal covering one day is sufficient in order to conduct a stress-analysis. The reason is that hypercortisolism and/or hypocortisolism with a duration of one day is indicative of burnout and/or chronic fatigue syndrome and/or their early stages. The reliability of the stress-analysis increases when a healthy state of a living being has been detected prior to hypercortisolism and/or hypocortisolism. By computing a skin conductance peak data signal over long-term periods, the processor thus enables long-term analysis about the living being's stress response behavior in the case of burnout and/or chronic fatigue. Increased reliability of the analysis can thus be achieved. In the systems known from prior art, only a "snapshot-analysis", which refers to punctual data, is possible. Such analysis, however, is not able to directly provide information on a developing status of burnout or chronic fatigue syndrome of a living being. In contrast to such systems, the processor according to the present invention is able to aid the user and/or a third party, such as a surgical or caregiver, to undertake measures according to the result of the long-term analysis. In particular, an upcoming full stage and/or recovery stage of burnout and/or chronic fatigue and/or a healthy stage can be detected so that intervention can be undertaken in time. This results possibly in reduced treatment duration, increased treatment effects and reduced costs.

Preferably, the processor can be integrated into a device including, but not exclusive to, a mobile device such as a cell phone, a smart phone, a tablet computer, a mobile mouse and/or mobile keyboard, a wearable device such as a watch, a device for being carried around a finger, a neck or at other part of a living being's body. Further, the processor can also be integrated into a stationary device such as a computer, a mouse and/or keyboard, a household apparatus such as a television, a refrigerator, a washing machine. In addition, the processor can be integrated into a household and/or office items such as desks, chairs, door handles, window handles, beds, clothes. Further, the processor can be integrated into any desirable and appropriate part of a vehicle such as a steering wheel, a seat, an infotainment system. Last but not least, the processor can also be connected to a network system such as a cloud system, a social network system, an intranet of a hospital.

In a preferred embodiment, the summation comprises determination of a cumulative sum of rising edges and/or a cumulative sum of peak heights and/or a rise time of said data peaks and/or a number of said data peaks per time unit. The rising edge is also known as positive edge and is defined as a change from low to high of a signal. The rise time of a data peak is the time frame in which a signal rises from a background value to the next peak. The advantage is that different ways of computing the skin conductance peak data signal are possible. Depending on the actual stress state and/or the requirements on the accuracy of the analysis, one can choose the appropriate way of computation to get the desired information about the living being.

Further preferably, the average value refers to a distribution of the number of the data peaks over a time segment comprising a plurality of the time units. The advantage is that it provides a data analysis based on skin conductance data from which long term statements about the stress response of the living being can be reliably made.

In another preferred embodiment, the upper threshold is at least twice as high as the lower threshold. The processor can thus distinguish reliably between exceeding of the skin conductance peak data signal resulting from burnout or chronic fatigue syndrome from that resulting from non-critical events such as party, funerals, disappointments, etc.

In another preferred embodiment, the output unit is configured to output the full stage signal when the average and/or absolute value of the skin conductance peak data signal falls to a minimum threshold, the minimum threshold being lower than said lower threshold. The lower threshold marks the lower bound of a healthy range of the skin conductance peak data defined as the range between the upper and the lower threshold. In this way it is able to detect a hypocortisolism succeeding from a hypercortisolism when the skin conductance peak data signal drops a certain amount below the healthy range of the living being. The full stage signal output in this way is thus more reliable.

In another preferred embodiment, the output unit is configured to output the full stage signal when the average and/or absolute value of the skin conductance peak data signal falls to the minimum threshold within a reference duration after the early stage of the predetermined stress state. The advantage is that the transition from a hypercortisolism to a hypocortisolism in which the skin conductance peak data signal crosses the afore-mentioned healthy range is further specified in correlation to a slope of the skin conductance peak data within the time window of the afore-mentioned transition which increases the accuracy of the outputting.

In another preferred embodiment, the output unit is configured to output the early stage signal and/or the full stage signal and/or the recovery stage signal and/or the healthy state signal only, when the respective condition for outputting the respective and/or the previous signal is given for a reference duration. This is particularly advantageous, since it further increases the reliability of the outputting of the different signals.

In another aspect of the invention, a processing method for processing skin conductance data of a living being is presented, the processing method comprising receiving a skin conductance data signal comprising a plurality of data peaks; computing a skin conductance peak data signal over a long-term period by deriving a feature related to said data peaks from said skin conductance data signal and forming a summation of said feature per time unit; and analyzing an average and/or an absolute value of said skin conductance peak data signal over at least a portion of said period to get information on at least one stage of burnout and/or chronic fatigue syndrome of said living being, outputting a full stage signal indicating a full stage of said predetermined stress state when the average and/or absolute value of said skin conductance peak data signal falls below a lower threshold after it has exceeded said upper threshold, and/or a recovery stage signal indicating a recovery stage when the average and/or absolute value of said skin conductance peak data signal rises towards and/or exceeds said lower threshold without exceeding said upper threshold after said full stage of said predetermined stress state, and/or a healthy state signal, when the average and/or absolute value of said skin conductance peak data signal is above said lower threshold and below said upper threshold.

In a further aspect of the invention, a device for detecting at least one stage of burnout and/or chronic fatigue syndrome of a living being is presented comprising at least one sensor configured to measure skin conductance data over time and a processor as claimed in claim 1 for processing said skin conductance data.

Advantageously, it is possible to both measure skin conductance data and to process these data using the device according to the present invention. This leads to more efficiency of detecting the different stages of burnout and/or chronic fatigue syndrome. Clinical measures such as intervention can be undertaken in time and the resulting expenses and complexity of treatment can be reduced.

In a preferred embodiment, the device is configured as a wearable device. Such a device can be worn at any part of the skin of the living being. In particular, it can be worn at the hand, the arm, the forehead and/or the neck of a human. A device wearable on the forehead can be exemplarily configured as a diadem. A wearable device provides a high degree of mobility and enables detecting the different stages of the stress state as well as the healthy state of the living being even when the living being is not stationary. Such a wearable device can be a watch, a device for being carried around a finger, a neck or at other part of a living being's body. Alternatively, such a wearable device can also be configured as or within a mobile device such as a cell phone, a smart phone, a tablet computer, a mobile mouse and/or mobile keyboard.

In yet a further aspect of the present invention there is provided a computer program comprising program code means for causing a computer to carry out the steps of the method as claimed in claim 7 when said computer program is carried out on said computer.

Another advantage of the present invention is that it is able to detect the initial stage of burnout or the chronic fatigue syndrome by detecting the condition of hypercortisolism, which is again possible by measuring and processing skin conductance data over time.

A further advantage of the invention is that an increased cortisol response to the stressor which imposes a burden on the individual can be avoided. Also, multiple cortisol determinations which are costly can be avoided.

Still further advantages of the present invention will be appreciated by those of ordinary skill in the art upon reading and understanding of the following detailed description.

Preferred embodiments of the invention are defined in the dependent claims. It shall be understood that the claimed methods, the claimed device and the claimed computer program have similar and/or identical preferred embodiments as the claimed processor and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

It is well known in the field of stress analysis that early burnout symptoms may be signaled by a hyperactivity of the HPA-axis, which in turn can be signaled by high salivary cortisol levels known as hypercortisolism. It is also known that an initial hyperactivity of the HPA-axis may develop into a hypoactivity as a response to chronic stress. Langelaan et al., "Do burned-out and work-engaged employees differ in the functioning of the hypothalamic-pituitary-adrenal axis?", Scand J Work Environ Health 32 (2006) 339-348 discloses a men-only study of the functioning of the HPA-axis for burnout, work-engaged and healthy reference managers. The study reveals only marginal differences in the functioning of the HPA-axis. In another study published by the same author, "Is Burnout Related to Allostatic Load?" International Journal of Behavioral Medicine 14 (2007) 213, no association is found on the relationship between allostatic load and burnout.

It is notable that this result is based on participants who are still at work and thus integrated in the employment process. The lack of differences in the functioning of the HPA-axis between burnout and healthy participants as well as the missing association between allostatic load and burnout are argued to be due to the process associated with hypocortisolism by Sonnentag et al., "Burnout and functioning of the hypothalamus-pituitary-adrenal axis there are no simple answers", Scand J Work Environ Health 32 (2006) 333-337. As a consequence, it is important to pay attention to the assessment of the situation of the cortisol sampling, taking into account the presence of acute stress, daily routine, and anticipated stress. The contribution of a chronic condition to the cortisol level may be hard to discriminate from temporary contributions.

Processors known for use in a device for detecting stress behavior of a living being, in particular for detecting burnout or chronic fatigue syndromes, are not able to detect an early stage of burnout or chronic fatigue syndrome of the living being. As a result, warning and treatment cannot be implemented in the early stage of the syndromes which lead to long treatment and high costs when a condition is treated in a later stage. In such situations, the burden on the individual as well as their family is rather heavy.

Figure 1:
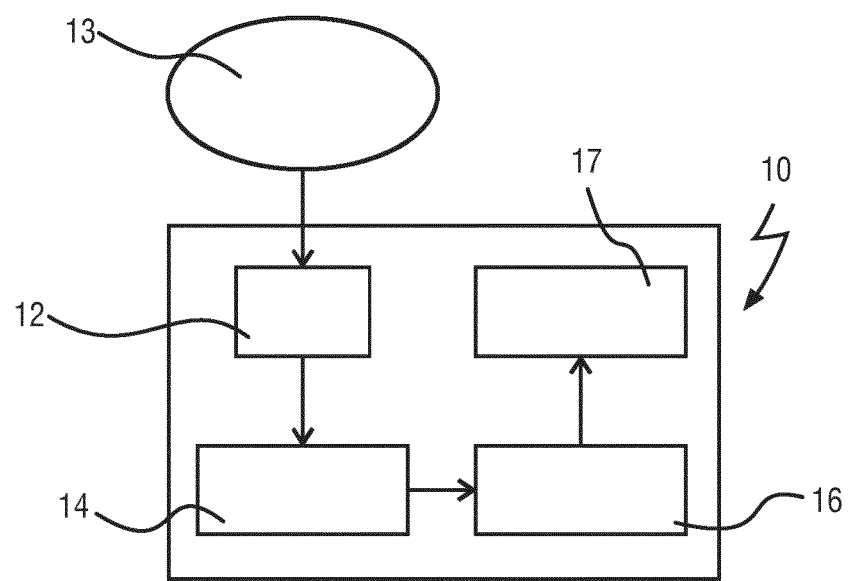
FIG. 1 shows a schematic block diagram of a processor according to the present invention.
Figure 2:
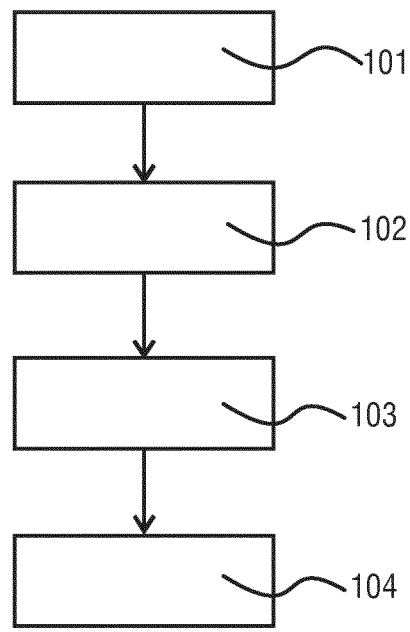
FIG. 2 shows in a schematic block diagram a processing method according to the present invention.

At least some of these problems are solved by the present invention. With reference to FIG. 1, an embodiment of a processor 10 is shown in a schematic block diagram for processing skin conductance data of a living being. The processing method corresponding to the processor 10 shown in FIG. 1 is illustrated in FIG. 2. The processor 10 comprises an input unit 12 for receiving a skin conductance data signal 13. This is carried out in step 101 of the method illustrated in FIG. 2. The skin conductance data signal 13 comprises a plurality of data peaks (indicated by the arrows in FIG. 5A). Such a skin conductance data signal 13 can be measured by a sensor, in particular a conductivity sensor, which measures the skin conductance of the living being over a period of time. The processor 10 further comprises a calculating unit 14 for computing a skin conductance peak data signal from the skin conductance data signal 13. This is carried out in step 102 of the method illustrated in FIG. 2. The skin conductance peak data signal is computed by a summation related to the data peaks of the skin conductance data signal 13. The data peaks of the skin conductance data signal 13 comprise a plurality of rising edges. The summation can therefore comprise determination of a cumulative sum of rising edges per time unit. Alternatively, the summation can also comprise determination of a number of the data peaks per time unit. The time unit is variable, i.e. a skin conductance peak data signal can be computed every minute, every five minutes or every hour, etc.

The processor 10 further comprises an analyzing unit 16 for analyzing the skin conductance peak data signal. This is carried out in step 103 of the method illustrated in FIG. 2. More precisely, the analyzing unit 16 analyzes an average and/or an absolute value of the skin conductance peak data signal in order to get information on burnout and/or chronic fatigue syndrome of the living being. This is preferably achieved by comparing the average and/or absolute value of the skin conductance peak data signal against at least one, further preferably at least two thresholds 22, 24, 26. The average value can be the arithmetic mean value, the median value or another statistical average value. Preferably, the processor 10 further comprises an output unit 17 for outputting at least one signal indicating a certain stage of a predetermined stress state. This is carried out in step 104 of the method illustrated in FIG. 2. The predetermined stress state can be burnout, chronic fatigue syndrome or any other stress-related syndrome.

Normally, a living being exposed to a stressor responds to the stressor by an active process known as allostasis. Over a sufficiently long period of time, the stress response can lead to a stress state, e.g. burnout or chronic fatigue syndrome. The stress state usually shows different stages of development. For instance, at the beginning of the stress state, it shows an early stage. If no measure is undertaken, the early stage proceeds into a full stage, where the stress state is fully developed. Either by means of the individual's own immune system or medical or surgical treatment, the stress state may be cured, arriving in a recovery stage. By defining appropriate thresholds 22, 24, 26, the analyzing unit 16 is able to detect changes of the skin conductance peak data signal relative to the thresholds 22, 24, 26, thus to identify in which stage of the stress state the living being is in at the time of analysis.

Another advantage of the processor 10 is that the skin conductance data can be easily measured by using a conductivity sensor. In particular, the skin conductance data are directly measurable on any part of the human skin such as the arm, the hands, the neck, the feet and the legs, etc. Another advantage of the processor 10 is that the computation of the skin conductance peak data signal is based on the plurality of data peaks comprised in the skin conductance data signal 13. The data peaks can be easily resolved so that the skin conductance peak data signal can be computed with high accuracy and sensitivity. Furthermore, such skin conductance data usually comprise a large amount of data peaks, especially when the individual is in a stress state. Hence, the skin conductance peak data signal computed in this way is highly reliable.

A further advantage of the processor 10 is that it provides different ways of analyzing the skin conductance peak data signal. Depending on the actual stress state and/or the requirements on the accuracy of the analysis, one can chose different information on stress behavior of the living being. In general, if acute changes of stress behavior of the living being need to be analyzed, the absolute value of the skin conductance peak data signal can be used; when an average stress behavior of the living being over a certain period of time is to be found, analyzing the average of the skin conductance peak data signal may be preferable. In a preferred embodiment, if the skin conductance peak data signal is computed by summation of the cumulative sum of rising edges, the absolute value of the skin conductance peak data signal is analyzed by the analyzing unit 16; if the skin conductance peak data signal is computed by summation of the number of data peaks, the average value is analyzed. Still a further advantage of the processor 10 is that it enables signaling of quantitative results from a stress analysis, so that the user or a third party is up-to-date about the development stage of the stress state and can undertake corresponding intervention measure based on the analysis.

Figure 3:
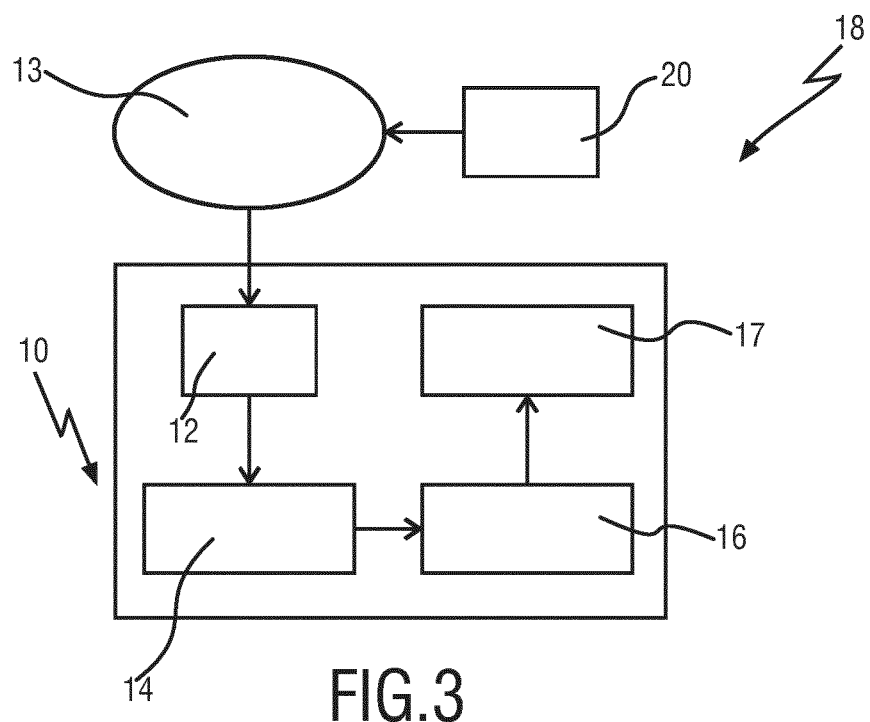
FIG. 3 shows in a schematic block diagram a device according to the present invention.
Figure 4:
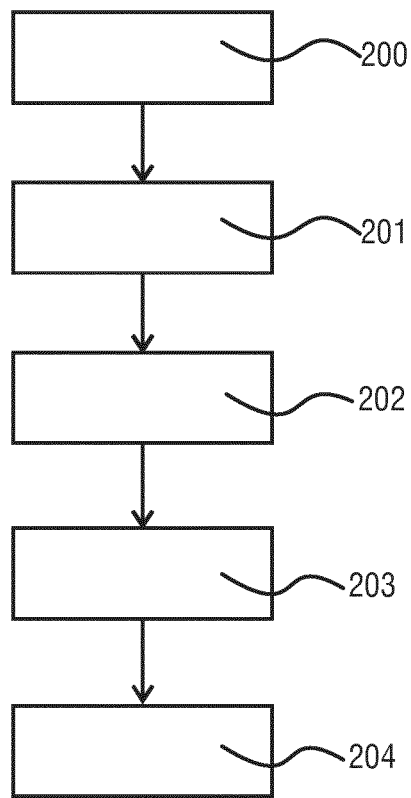
FIG. 4 shows in a schematic block diagram a method according to the present invention.

With reference to FIG. 3, a device 18 for detecting a stress behavior of a living being is shown in a schematic block diagram. A method for detecting stress behavior of a living being corresponding to the device 18 in FIG. 3 is schematically shown in FIG. 4. The device 18 comprises at least one sensor unit 20 for measuring skin conductance data of the living being over a period of time. The measuring is done in step 200 of the method illustrated in FIG. 4. The sensor unit 20 is preferably configured as a galvanic conductivity sensor which is able to measure the conductivity of the skin of the living being. The device 18 comprises a processor 10, preferably configured as shown in FIG. 1, for processing the skin conductance data in steps 201 to 204 of the method illustrated in FIG. 4.

The device 18 can be preferably configured as a wearable device. When a device is worn over a long period of time, the skin conductance data can be measured over the long period so that these data can be processed in order to get accurate information on stress behavior of the living being. In a preferred embodiment of the device 18, the skin conductance data signal 13 and/or the skin conductance peak data signal can be monitored. In this way, changes of the monitored signal can be followed up efficiently. This provides the opportunity of sending a warning signal to the wearer of the device 18 and/or a third party, such as a doctor or a caregiver. It is also advantageous since intervention is possible in different stages of the stress state, especially in the early stage. Both long term and short term effects of the intervention can be monitored by the wearable device 18.

Furthermore, it is a general advantage of the device 18 that it is able to measure and make use of skin conductance data. It is particularly efficient to use such data in order to detect changes in the stress response of an individual. The stress response causes the activation of the autonomic nervous system, which is communicated via the vagal nerve into several body parts. Specifically, the sweat glands in the palmar region, as well as on the skin of the wrist are activated. This mechanism results in an increase of the skin conductance. By detecting and monitoring the skin conductance in an unobtrusive way, the device 18 thus provides easy access to the activity of the HPA-axis, hence the stress state of the individual.

Figure 5:
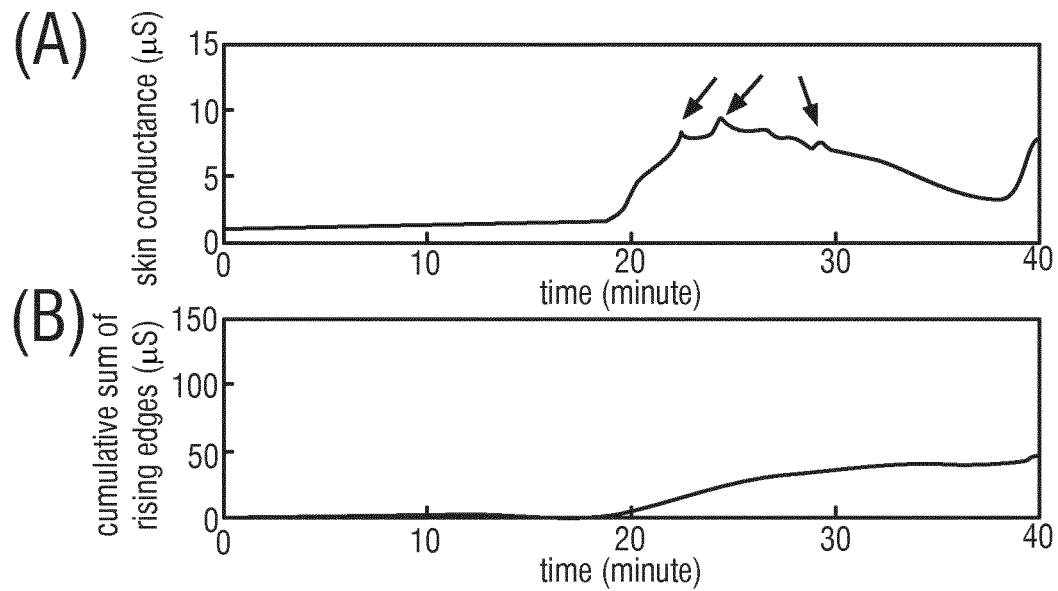
FIG. 5A shows a first example of a measurement of skin conductance data signal.
FIG. 5B shows a first example of a skin conductance peak data signal computed from the skin conductance data signal in FIG. 5A.

With reference to FIG. 5, a first example of the skin conductance data signal and the skin conductance peak data signal are shown each in a graph. FIG. 5A shows a skin conductance graph, in which a measurement of the skin conductance (vertical axis) of an individual over a period of 40 minutes (horizontal axis) is presented. The unit for the vertical axis is chosen to be µS, while the unit for the horizontal axis is minute. As can be seen from the skin conductance graph, the skin conductance data signal show essentially a smooth line in the first half of the measurement while a plurality of data peaks (indicated by arrows) are seen in the second half of the measurement. The occurrence of data peaks means that the individual shows stress response in the second half of the measurement period. This stress response causes the activation of the autonomic nervous system, which is communicated via the vagal nerve into different body parts of the individual, such as the sweat glands in the palmar region as well as the skin of the wrist. The stress response results in changes of the skin conductance of the individual, which can be detected by a sensor, preferably by the sensor unit 20 of the device 18 shown in FIG. 3. The sensor unit 20 is preferably able to measure skin conductance with high sensitivity. In particular, the sampling rate of the sensor unit 20 can be varied over a large range so that depending on the actual requirements in the application the number of data points for a fixed measurement period can be varied. It is noted that the skin conductance data signal presented in FIG. 5A is to be considered only qualitatively. In general, a skin conductance graph can also show a different form with more or fewer fluctuations than shown here.

In a preferred embodiment, the input unit 12 and/or the calculating unit 14 is configured to distinguish between data peaks in the skin conductance data signal resulting from one or more stages of a stress state, e.g. burnout or chronic fatigue, from peaks that result from other mechanisms or events. It is generally known that motion artifacts and thermal regulation can also lead to data peaks. It is also known that the data peaks related to the stress state is associated with a slope, wherein the slope falls in a limited range. Motion artifacts cause a slope that is above this limited range, whereas thermal regulation causes a slope below this limited range. The limited range can preferably be predetermined by the input unit 12 and/or the calculating unit 14. By determining the slope of data peaks and comparing the slope against the limited range, the processor 10 and/or the device 18 thus enables a reliable processing of skin conductance data signal.

FIG. 5B shows a skin conductance peak graph in which the cumulative sum of rising edges (vertical axis) is plotted over a period of 40 minutes (horizontal axis), thus showing how the skin conductance peak data signal has evolved over the measurement period in FIG. 5A. It is noted that the skin conductance peak data signal presented in FIG. 5B is to be considered only qualitatively. In general, a skin conductance peak graph can also show a different form with more or fewer fluctuations than shown here. The same units are used here as in FIG. 5A. It is noted that in general it is not necessary that the period over which the skin conductance peak data signal is calculated is the same as the aforementioned measurement period. Each data peak of the skin conductance data shown in FIG. 5A comprises at least one rising edge, which is an indication of changes in the slope of the skin conductance. The calculating unit 14 can compute the cumulative sum of the rising edges of the data peaks per time unit, for instance 10 minutes. This is, however, non-restricting and different time units can be chosen. As can be seen in the skin conductance peak graph in FIG. 5B, the skin conductance peak data signal shows a flat line in the first 20 minutes which is essentially at 0 µS. This corresponds to the first half of the measurement of the skin conductance data shown in FIG. 5A where the individual hardly shows any stress response. In the following 20 minutes, the skin conductance peak data signal shows a gradual increase followed by a saturation. The increase corresponds to the part of the skin conductance data (roughly between 20 minutes and 30 minutes), in which a multiplicity of data peaks can be observed. In this part, the individual shows an active stress response. When the number of data peaks per time unit saturates, the skin conductance peak data signal also shows saturation.

It is advantageous to compute the skin conductance peak data signal by determination of a cumulative sum of rising edges per time unit. The change of skin conductance of an individual is an indicator for his/her stress response. Nevertheless, the information one gains directly from the skin conductance data signal is limited. To the contrary, the cumulative sum of rising edges of data peaks reflects how both the strength and the frequency with which a living being responds to stressors, thus providing more reliable information about the stress response of the living being. By varying the time unit, acute changes as well as average changes in the stress behavior are accessible. Alternatively, the skin conductance peak data signal can also be computed by determination of a cumulative sum of peak heights and/or a rise time of said data peaks and/or a number data peaks per time unit and/or other quantities related to the data peaks of the corresponding skin conductance data signal.

Figure 6:
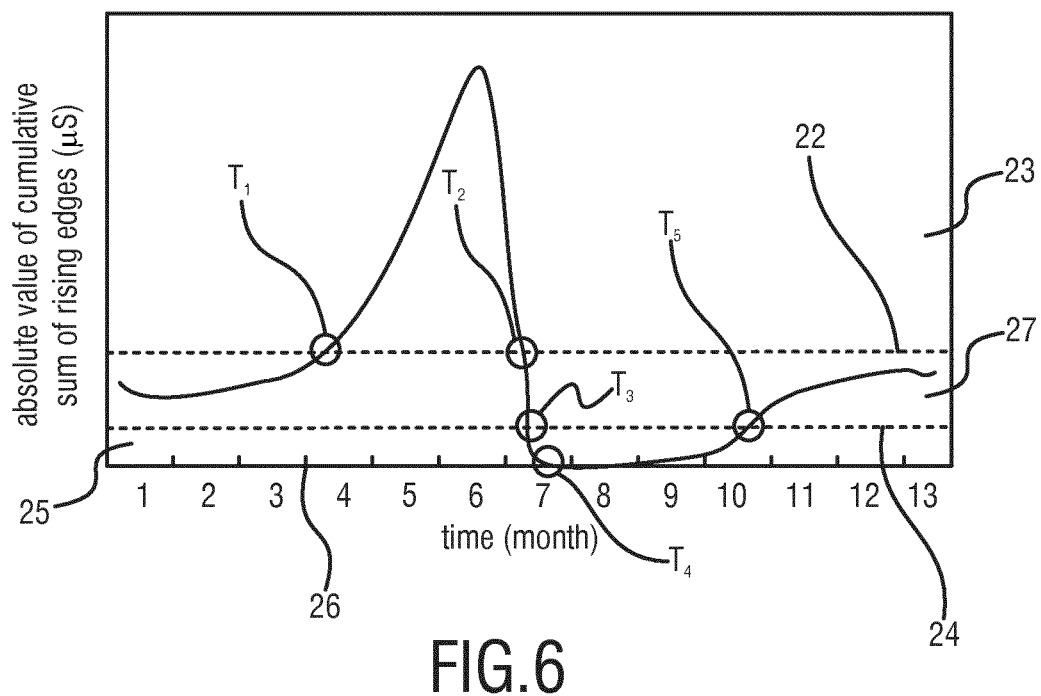
FIG. 6 shows a first example of an analysis of a skin conductance peak data signal.

FIG. 6 shows a first example of an analysis of an absolute value (vertical axis) of a skin conductance peak data signal over a period of thirteen months (horizontal axis). Similar to FIG. 5B, the skin conductance peak data signal in FIG. 6 is also calculated by determination of the cumulative sum of rising edges per time unit. Here, the time unit is chosen to be a day. This means that the skin conductance peak data signal is computed on a daily basis by cumulatively summing up the rising edges from the corresponding skin conductance data signal. It is noted that for plausibility reasons, the horizontal axis is shown in months. It is also noted that the unit for the vertical axis is µS, while the scale for the vertical axis is not shown. Both the unit and the scale for the vertical axis can be appropriately chosen depending on the actual skin conductance peak data signal being analyzed. Furthermore, it is noted that the skin conductance peak data signal presented in FIG. 6 is to be considered only qualitatively and is shown in a smoothed form. These fluctuations have been omitted in FIG. 6 to better illustrate the relevant details. In particular, an analysis graph can show a different form with more or fewer fluctuations than shown here, i.e. in practice the skin conductance peak data signal will generally show many fluctuations around the smoothed curve as shown in FIG. 6. In a preferred embodiment, the analyzing unit 16 is configured to compare the absolute value of the skin conductance peak data signal against at least one threshold, in particular against two different thresholds.

As can be seen in the analysis graph of FIG. 6, the analyzing unit 16 defines an upper threshold 22 and a lower threshold 24. Then, the analyzing unit 16 compares the skin conductance data peak signal against the upper threshold 22 and the lower threshold 24. The upper threshold 22 is chosen such that when the absolute value of the skin conductance peak data signal exceeds the upper threshold 22, the individual is in an early stage of a stress state. Above the upper threshold 22, the individual is over-sensitive to stressors. The range of the graph above the upper threshold 22 is thus identifiable as an over-sensitive range 23. The stress state is predetermined to be a specific stress state such as burnout syndrome or chronic fatigue syndrome. Depending on the choice of the stress state, the upper threshold 22 can take different values. Preferably, the output unit 17 of the processor 10 and/or the device 18 is configured to output an early stage signal indicating the early stage of the predetermined stress state, when the absolute value of the skin conductance peak data signal exceeds the upper threshold 22. This exceeding results from a hypercortisolism in the activity of the HPA-axis. Preferably, the device 18 can further comprise a communication unit, which communicates the early stage signal with a communication system, preferably an external communication system such as a data network in a hospital, a recovery station and/or the internet. The early stage signal can also be sent via an interface to a third party such as a caregiver or a doctor.

Similar to the upper threshold 22, the lower threshold 24 is chosen such that, when the absolute value of the skin conductance peak data signal falls below the lower threshold 24, the individual is in a full stage of the stress state. Below the lower threshold 24, the individual is hardly responding to stressors. The range of the graph below the lower threshold 24 is thus identifiable as a non-response range 25. The output unit 17 is preferably configured to output a full stage signal indicating the full stage of the predetermined stress state, when the absolute value of the skin conductance peak data signal falls below the lower threshold 24, after it has exceeded the upper threshold 22. In a preferred embodiment, the full stage signal is output only, when the absolute value of the skin conductance peak data signal falls to a minimum threshold 26 which is lower than the lower threshold 24 by a certain amount. It is noted that the minimum threshold 26 in FIG. 6 does not necessarily correspond to the value of zero along the vertical axis, while this value is a possible one.

The range between the lower threshold 24 and the upper threshold 22 is identifiable as a healthy range 27, in which the individual shows normal stress response. The output unit 17 is preferably configured to output a healthy state signal when the absolute value of the skin conductance peak data signal is above the lower threshold 24 and below the upper threshold 22.

After the early stage or the full stage of the predetermined stress state, when the absolute value of the skin conductance peak data signal rises again and exceeds the lower threshold 24, the individual starts to show recovery from the stress state. The output unit 17 is preferably configured to output a recovery stage signal indicating the recovery stage of the predetermined stress state when absolute value of the skin conductance peak data signal exceeds the lower threshold 24 without exceeding the upper threshold 22, after the early stage signal or the full stage signal has been output by the output unit 17.

It is advantageous to configure the output unit 17 to output the afore-mentioned different signals indicating each a different stage of the predetermined stress state. An individual shows stress response either due to his living environment or due to neurological, physiological or psychological reasons. If he/she wears the wearable device 18 for a period of time that is sufficiently long, for instance over a year, the progressing of his stress response can be acquired and investigated. Such information may be helpful to find out characteristic stress behavior of the individual as well as to undertake the necessary measures, such as intervention and treatments. In particular, it is able to undertake such measures as soon as possible, for instance after the output unit 17 has output the early stage signal. Surgical persons and/or caregivers can counteract against the predetermined stress state of the individual in an early state, which reduces the length and costs of treatments significantly. Besides the financial aspect, the burden on the individual as well as his family will also be reduced significantly. Furthermore, treating a predetermined stress date, in particular burnout or chronic fatigue syndrome, in an early stage is generally much easier where less chance of secondary effects is expected compared to a later stage.

A further advantage of the processor 10 and the device 18 is that it enables a following-up of the individual's stress response over a long period of time. Different individuals respond differently to the same stressors. Consequently, different skin conductance data can be measured showing different data peaks. Hence, for the sake of reliable analysis, different upper, lower and minimum thresholds 22, 24, 26 need to be defined for different individuals. Based on an analysis conducted over a sufficiently long period of time, the upper, lower and minimum thresholds 22, 24, 26 can be defined accurately and reliably for the individual.

In a preferred embodiment, the analyzing unit 16 is configured to define different points in time which correspond to the moments at which the absolute value of the skin conductance peak data signal shows a specific behavior. As can be seen in the analysis graph of FIG. 6, a first point of time $T_1$ is defined as the moment at which the absolute value of the skin conductance peak data signal exceeds the upper threshold 22. A second point of time $T_2$ is defined as the moment at which the absolute value of the skin conductance peak data signal falls below the upper threshold 22 some time after $T_1$. A third point of time $T_3$ is defined as the moment at which the absolute value of the skin conductance peak data signal falls below the lower threshold 24 some time after $T_2$. A fourth point of time $T_4$ is defined as the moment at which the absolute value of the skin conductance peak data signal falls to the minimum threshold 26 some time after $T_3$. A fifth point of time $T_5$ is finally defined as the moment at which the absolute value of the skin conductance peak data signal exceeds the lower threshold 24 some time after $T_4$.

Between the time points $T_1$ and $T_2$, the output unit 17 thus outputs the early stage signal. The stress response of the individual is in the over-sensitive range 23. The duration of the early stage of the predetermined stress state can thus be determined as $$\Delta T_{early} = T_2 - T_1.$$

Between $T_2$ and $T_3$, the stress response of the individual is in the healthy range 27. Between $T_3$ and $T_5$, preferably between $T_4$ and $T_5$, the output unit 17 outputs the full stage signal. The stress response of the individual is in the non-response range 25. Hence, the duration of the full stage of the predetermined stress state can be determined as:

$$\Delta T_{full} = T_5 - T_3$$

or preferably $$\Delta T_{full} = T_5 - T_4.$$

The amount of time which the predetermined stress state has taken to reach the full stage after the early stage can thus be determined as:

$$\Delta T_{early-full} = T_3 - T_2$$

or preferably $$\Delta T_{early-full} = T_4 - T_2.$$

In many cases, a hyperactivity of the HPA-axis or hypercortisolism can be only surely identified for an individual responding to a stressor after his/her stress response has been in the over-sensitive range for a certain amount of time. After the hyperactivity, a hypoactivity of the HPA-axis or hypocortisolism can only be surely identified after his/her stress response has been in the non-response range for a certain amount of time.

In order to take this into account and to increase the accuracy and reliability of the output signals, the analyzing unit 1 is preferably configured to count the following durations: $\Delta T_{over-sensitive}$, which marks the duration starting from $T_1$ as long as the absolute value of the skin conductance peak data signal is in the over-sensitive range; $\Delta T_{non-response}$, which marks the duration starting from $T_3$, preferably starting from $T_4$, as long as the absolute value of the skin conductance peak data signal is in the non-response range. The analyzing unit 16 compares the afore-mentioned durations $\Delta T_{over-sensitive}$ and $\Delta T_{non-response}$ each against a reference duration $\Delta T^*_{over-sensitive}$ and $\Delta T^*_{non-response}$, respectively. The output unit 17 is configured such that it outputs the early stage signal only when the condition $\Delta T_{over-sensity} \geq \Delta T^*_{over-sensitive}$ is fulfilled. Also, the output unit 17 is configured such that it outputs the full stage signal only when the condition $\Delta T_{over-sensitive} \geq \Delta T^*_{over-sensitive}$ and $\Delta T_{non-response} \geq \Delta T^*_{non-response}$ is fulfilled. By assigning sufficiently large values for the reference durations $\Delta T^*_{over-sensitive}$ and $\Delta T^*_{non-response}$, false signals can be effectively avoided.

The output unit 17 is preferably configured to output the full stage signal only when the condition $\Delta T_{early-full} \leq \Delta T^*_{early-full}$ is fulfilled. Since the absolute value of the skin conductance peak data signal traverses the healthy range between the early stage and the full stage of the stress state, it can be avoided in this way that the intermediate range is misinterpreted as the healthy range or the intermediate stage of the stress state is misinterpreted as the healthy state.

Figure 7:
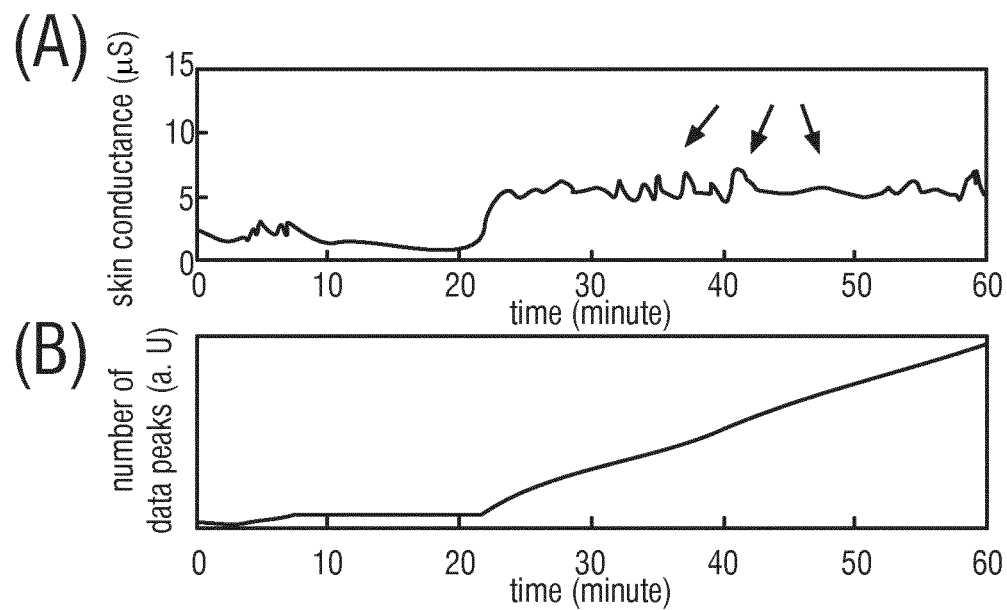
FIG. 7A shows a second example of a measurement of skin conductance data signal.
FIG. 7B shows a second example of a skin conductance peak data signal computed from the skin conductance data signal in FIG. 7A.

With reference to FIG. 7, a second example of the skin conductance data signal and the skin conductance peak data signal are shown each in a graph. FIG. 7A shows a skin conductance graph, which shows a measurement of the skin conductance (vertical axis) of an individual over a measurement period of 60 minutes (horizontal axis). It is noted that the skin conductance data signal presented in FIG. 7A is to be considered only qualitatively. In general, a skin conductance graph can also show a different form with more or fewer fluctuations than shown here. The unit for the vertical axis is µS while it is minute for the horizontal axis. As can be seen from the skin conductance graph, the skin conductance data signal shows in the first 20 minutes of the measurement relatively few data peaks while the number of data peaks (indicated by the arrows in FIG. 7A) drastically increases in the rest of the measurement. This is accompanied by an increase of the skin conductance measured by the sensor unit 20. The increase of the number of data peaks indicate that the individual shows a more active stress response in the last 40 minutes of the measurement period.

FIG. 7B shows a skin conductance peak graph in which the number of data peaks per time unit (vertical axis) is plotted over a period of 60 minutes (horizontal axis). The unit for the vertical axis is arbitrary while it is minute for the horizontal axis. The analysis graph thus shows how the skin conductance peak data signal has evolved over the same period as the afore-mentioned measurement period in FIG. 7A. The skin conductance peak data signal is computed by the calculating unit 14 shown in FIG. 1 and FIG. 3 based on the skin conductance data signal shown in FIG. 7A. In particular, the skin conductance peak data signal shown in FIG. 7B is computed by determination of the number of data peaks per time unit, for instance per minute. It is noted that the skin conductance peak data signal presented in FIG. 7B is to be considered only qualitatively. In general, a skin conductance peak graph can also show a different form with more or fewer fluctuations than shown here. As can be seen in the skin conductance peak graph in FIG. 7B, the skin conductance peak data signal shows essentially a flat line in the first 20 minutes (roughly between 0 and 20 minutes) which is close to 0 µS. This corresponds to the first 20 minutes of the measurement of the skin conductance data shown in FIG. 7A where the individual hardly shows any stress response. In the following 40 minutes, the skin conductance peak data signal shows a gradual increase. The increase corresponds to the last 40 minutes of the measurement shown in FIG. 7A, where an increase of the number of data peaks can be observed. In this part, the individual shows a relatively active stress response.

Figure 8:
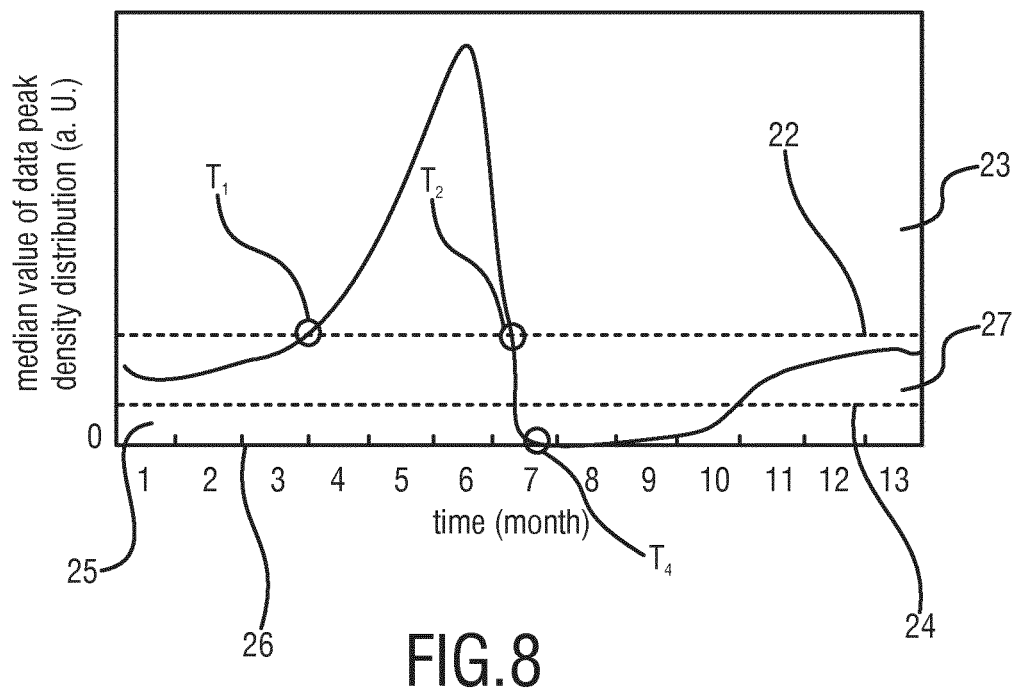
FIG. 8 shows a second example of an analysis of a skin conductance peak data signal.

With reference to FIG. 8, an analysis of an average value (vertical axis) of a skin conductance peak data signal over a period of thirteen months (horizontal axis) is shown in an analysis graph. The skin conductance peak data signal is also calculated by determination of the number of data peaks per time unit. It is noted that the unit for the vertical axis is arbitrary, while the scale (not shown) can be appropriately chosen depending on the actual skin conductance peak data to be analyzed. It is also noted that the horizontal axis is shown in month for plausibility reasons. Furthermore, it is noted that the skin conductance peak data signal presented in FIG. 8 is to be considered only qualitatively, i.e. a smoothed version (without the generally existing fluctuations around the smoothed curve) is shown. In general, an analysis graph can also show a different form with more or fewer fluctuations than shown here. The average value is preferably a median value and refers to a distribution of data peak density (DPD) over a time segment. For this preferred embodiment, the DPD is defined as the number of data peaks per time unit, for instance per minute. This means that the DPD is a measure for the frequency of the data peaks. The calculating unit 14 divides the period, in which the skin conductance peak data signal is calculated, into a plurality of time segments, wherein each time segment comprises a plurality of time units. For instance, if the skin conductance peak data signal is calculated for 1 year, the time segment can be exemplarily set to be 1 day, 5 hours or 30 minutes. Further, the calculating unit 16 determines a distribution of the DPD over each time segment. Such a distribution is in general describable by a distribution function, e.g. a Gaussian function, a probability density function (pdf), a probability mass function (pmf), a normal distribution function or a random distribution function. Such a distribution function comprises an average value, in particular a median value. This median value is plotted finally as a function of the time segments over the period of a year.

The device 18 and processor 20 thus provide a second possibility of obtaining information on at least one stress state of a living being. Preferably, they enable determining an average value, preferably a median value of the DPD distribution over a period in which the individual shows the healthy state. This median value can be taken as the lower threshold 24 which marks the boundary of the healthy range of the analysis graph of the individual. Similarly to the analysis graph shown in FIG. 6, the different thresholds 22, 24, 26 can be defined by the analyzing unit 16 appropriately for the analysis graph in FIG. 8. The output unit 17 is configured to preferably output the early stage signal and/or the full stage signal and/or the recovery stage signal and/or the healthy state signal when the respective condition for outputting the respective signal is given. Furthermore, the analysis graph in FIG. 8 can be divided into the different ranges 23, 25, 27 in analogy to FIG. 6 and the different points of time $T_1$ to $T_5$ can also be determined correspondingly. Additionally, the different durations $\Delta T_{early}$, $\Delta T_{full}$, $\Delta T_{early-full}$, $\Delta T_{over-sensitive}$, $\Delta T_{non-response}$ and reference durations $\Delta T^*_{over-sensitive}$ and $\Delta T^*_{non-response}$ can also be determined or predetermined, respectively. Accordingly, all the effects and advantages achievable by determining the aforementioned durations as described in respect of the absolute value of the skin conductance peak data signal can also be achieved in the case of the average, preferably the median value of the skin conductance peak data signal.

In a preferred embodiment, the output unit 17 is configured to output the early stage signal when the average value, further preferably the median value of the skin conductance peak data signal is at least twice as determined while the individual shows the healthy state. This can be realized by defining the upper threshold 22 to be essentially twice the lower threshold 24. The ratio between the upper threshold 22 and the lower threshold 24 can be in general set to any appropriate ratio so that the early stage signal can be output when the average value, preferably the median value of the skin conductance peak data signal has increased over the lower threshold by this ratio.

Further preferably, the output unit 17 is configured to output the full stage signal only when the average value, preferably the median value of the skin conductance peak data signal falls to close to zero within a short time and stays there for a certain time period. For this purpose, the analyzing unit 16 defines the minimum threshold 26 to be essentially zero, as indicated by the number 0 at the bottom of the vertical axis of FIG. 8. Furthermore, it compares the duration $\Delta T_{early-full}$ against a reference duration $\Delta T^*_{early-full}$. The duration $\Delta T_{early-full}$ is the duration of a transition stage from the early stage to the full stage of the stress state of a living being. Within $\Delta T_{early-full}$, the skin conductance peak data signal undergoes a transition from the over-sensitive range to the non-response range of the analysis graph. Typically, the reference duration $\Delta T^*_{early-full}$ is set to be 2 days or less. The output unit 17 only outputs the full stage signal when the condition $\Delta T_{early-full} \leq \Delta T^*_{early-full}$ is fulfilled. In addition, the analyzing unit 16 counts a duration $\Delta T_{minimum}$ starting from the time point $T_4$. Within the duration $\Delta T_{minimum}$, the average value, preferably the median value of the skin conductance peak data signal remains essentially at or below the minimum threshold 26. The analyzing unit 16 then compares $\Delta T_{minimum}$ with a reference duration $\Delta T^*_{minimum}$ while counting. The output unit 17 only outputs the full stage signal when the condition $\Delta T_{minimum} \geq \Delta T^*_{minimum}$ is fulfilled.

While the invention has been illustrated and described in detail in the drawings and foregoing description, such illustration and description are to be considered illustrative or exemplary and not restrictive. In particular, the curves shown in FIG. 5A to FIG. 8 only present each a qualitative behavior of the plotted skin conductance data signal or skin conductance peak data signal. These curves are not to be considered as a quantitative representation of measurements/calculations/analysis in real application of the processor and/or device according to the present invention. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for processing skin conductance data of a living being, the device comprising:
   a conductivity sensor, wherein the conductivity sensor is configured to measure skin conductance data over time;
   a processor circuit,
      wherein the processor circuit is configured to receive the measured skin conductance data,
      wherein the measured skin conductance data comprises a plurality of data peaks,
      wherein the processor circuit is configured to compute a skin conductance peak data signal over a period of at least one day by deriving a cumulative sum of rising edge values,
      wherein the cumulative sum of rising edge values is related to said plurality of data peaks,
      wherein the processor circuit is configured to form a summation of said cumulative sum of rising edge values per time unit,
      wherein the processor circuit is configured to analyze an absolute value of said skin conductance peak data signal over at least a portion of said period to identify one of three stages of a predetermined stress state of said living being,
      wherein the processor circuit is configured to compare the absolute value of said skin conductance peak data signal against a lower threshold and an upper threshold, and
      wherein the processor circuit is configured to output a full stage signal indicating a full stage of said predetermined stress state when the absolute value of said skin conductance peak data signal falls below the lower threshold after it has exceeded said upper threshold,
      wherein the processor circuit is configured to output a recovery stage signal indicating a recovery stage when the absolute value of said skin conductance peak data signal exceeds said lower threshold without exceeding said upper threshold after said full stage of said predetermined stress state, and wherein the processor circuit is configured to output a healthy state signal, when the absolute value of said skin conductance peak data signal is above said lower threshold and below said upper threshold.

2. The device according to claim 1, wherein the processor circuit is configured to output said full stage signal when the absolute value of said skin conductance peak data signal falls to a minimum threshold, and
wherein said minimum threshold is lower than said lower threshold.

3. The device according to claim 2, wherein the processor circuit is configured to output said full stage signal when the absolute value of said skin conductance peak data signal falls to said minimum threshold within a reference duration after said early stage of said predetermined stress state.

4. The device according to claim 1, wherein the processor circuit is configured to output said full stage signal, said recovery stage signal, and said healthy state signal only when the respective condition for outputting the respective and a previous signal is given for a reference duration.

5. A method for processing skin conductance data of a living being, comprising:
measuring, with a conductivity sensor, skin conductance data over time;
receiving, with a processor, the measured skin conductance data signal, wherein the measured skin conductance data comprises a plurality of data peaks;
computing, with the processor, a skin conductance peak data signal over a period of at least one day by deriving a cumulative sum of rising edge values, wherein the cumulative sum of rising edge values is related to said plurality of data peaks;
forming, with the processor, a summation of said cumulative sum of rising edge values per time unit;
analyzing, with the processor, an absolute value of said skin conductance peak data signal over at least a portion of said period to identify one of three stages of a predetermined stress state of said living being; and
comparing, with the processor, the absolute value of the skin conductance peak data signal against a lower threshold and an upper threshold;
outputting, with the processor, a full stage signal indicating a full stage of said predetermined stress state when the absolute value of said skin conductance peak data signal falls below the lower threshold after it has exceeded said upper threshold;
outputting, with the processor, a recovery stage signal indicating a recovery stage when the absolute value of said skin conductance peak data signal exceeds said lower thresholds without exceeding said upper threshold after said full stage of said predetermined stress state; and
outputting, with the processor, a healthy state signal, when the absolute value of said skin conductance peak data signal is above said lower threshold and below said upper threshold.

6. The device according to claim 1, wherein said device is configured as a wearable device.

7. A non-transitory machine-readable medium encoded with instructions for execution by a processor circuit for processing skin conductance data of a living being, the non-transitory machine-readable medium comprising:
instructions for measuring, with a conductivity sensor, skin conductance data over time;
instructions for receiving, with the processor circuit, the measured skin conductance data signal, wherein the measured skin conductance data comprises a plurality of data peaks;
instructions for computing, with the processor circuit, a skin conductance peak data signal over a period of at least one day by deriving a cumulative sum of rising edge values, wherein the cumulative sum of rising edge values is related to a plurality of data peaks, wherein the plurality of data peaks are from a received skin conductance data signal;
instructions for forming, with the processor circuit, a summation of said cumulative sum of rising edge values per time unit;
instructions for analyzing, with the processor circuit, an absolute value of said skin conductance peak data signal over at least a portion of said period to identify one of three stages of a predetermined stress state of said living being;
instructions for comparing, with the processor circuit, the absolute value of the skin conductance peak data signal against a lower threshold and an upper threshold;
instructions for outputting, with the processor circuit, a full stage signal indicating a full stage of said predetermined stress state when the absolute value of said skin conductance peak data signal falls below lower threshold after it has exceeded said upper threshold; and
instructions for outputting, with the processor circuit, a recovery stage signal indicating a recovery stage when the absolute value of said skin conductance peak data signal exceeds said lower threshold without exceeding said upper threshold after said full stage of said predetermined stress state; and
instructions for outputting, with the processor circuit, a healthy state signal, when the absolute value of said skin conductance peak data signal is above said lower threshold and below said upper threshold.

8. The non-transitory machine-readable medium according to claim 7, wherein the instructions for computing the skin conductance peak data signal further comprise:
instructions for determining a cumulative sum of peak heights, a rise time of said data peaks, and a number of said data peaks per time unit.

9. The non-transitory machine-readable medium according to claim 8, wherein said average value refers to a distribution of said number of said data peaks over a time segment comprising a plurality of said time units.

10. The non-transitory machine readable medium according to claim 7, wherein the instructions for outputting are configured to output said full stage signal when the at least one of average and absolute value of said skin conductance peak data signal falls to a minimum threshold, said minimum threshold being lower than said lower threshold.

11. The non-transitory machine-readable medium according to claim 10, wherein the instructions for outputting are further configured to output said full stage signal when the absolute value of said skin conductance peak data signal falls to said minimum threshold within a reference duration after said early stage of said predetermined stress state.

12. The non-transitory machine-readable medium according to claim 7, wherein the instructions for outputting are further configured to output an early stage signal when the absolute value of the skin conductance peak data signal exceeds the upper threshold.

13. The non-transitory machine-readable medium according to claim 7, wherein the instructions for outputting are further configured to output at least one of said full stage signal, said recovery stage signal, and said healthy state signal only when the respective condition for outputting at least one of the respective and the previous signal is given for a reference duration.

14. The device according to claim 1, wherein the processor circuit is further configured to output an early stage signal when the absolute value of the skin conductance peak data signal exceeds the upper threshold.

15. The method according to claim 5, further comprising:
   outputting an early stage signal when the absolute value of the skin conductance peak data signal exceeds the upper threshold.

16. The method according to claim 5, wherein the computing the skin conductance peak data signal further comprises:
   determining a cumulative sum of peak heights, a rise time of said data peaks, and a number of said data peaks per time unit.

17. The method according to claim 16, wherein said average value refers to a distribution of said number of said data peaks over a time segment comprising a plurality of said time units.

* * * * *